United States Patent [19]

Green et al.

[11] 4,327,738
[45] May 4, 1982

[54] ENDOSCOPIC METHOD & APPARATUS INCLUDING ULTRASONIC B-SCAN IMAGING

[76] Inventors: Philip S. Green, 60 MacBain Ave.; Dilip G. Saraf, 98 Euclid Ave., both of Atherton, Calif. 94025; James F. Havlice, 348 Toyon Ave., Los Altos, Calif. 94022

[21] Appl. No.: 86,354

[22] Filed: Oct. 19, 1979

[51] Int. Cl.³ .............................................. A61B 10/00
[52] U.S. Cl. ......................................... 128/660; 128/6
[58] Field of Search ................................ 128/660–663, 128/6, 8; 73/626, 642, 644; 358/98

[56] References Cited

U.S. PATENT DOCUMENTS

| | | | |
|---|---|---|---|
| 3,387,609 | 6/1968 | Erikson | 73/642 X |
| 3,779,234 | 12/1973 | Eggleton et al. | 128/660 |
| 3,936,791 | 2/1976 | Kossoff | 128/660 X |
| 3,938,502 | 2/1976 | Bom | 128/660 |
| 3,942,530 | 3/1976 | Northered | 128/4 |
| 4,204,528 | 5/1980 | Termanini | 128/6 |
| 4,217,516 | 8/1980 | Iinuma et al. | 128/660 |

FOREIGN PATENT DOCUMENTS

| | | | |
|---|---|---|---|
| 2305501 | 8/1974 | Fed. Rep. of Germany | 128/660 |
| 387698 | 9/1973 | U.S.S.R. | 128/660 |

OTHER PUBLICATIONS

Ikukoshi, Y., "Apparatus for Endoscopic and Ultrasonic Medical Diagnosis" Jap. Publ. Unexamined Pat. Appl. No. P. Sho-52/67104, Publ. Jan. 9, 1979.
Taylor, W. B. et al, "A High-Resolution Trans-Rectal Ultrasonographic System," UTS in Med & Biol. vol. 5, pp. 129-138 Pergarmmon Press 1979.
Histand, M. B. et al, "UTS Palsed Doppler Transesophageal Measurement of Aortic Haeniodymamics in Humans," *Ultrasonics* Sep. 1979.
Lutz, H. et al., "Transgastroscopic Ultrasonography," *Endoscopy* 8 (1976), pp. 203-205.
Hisanaga, K. et al, "A New Trans-Digestive Tract Scanner With A Gastro-Fiberscope," Proc. 23rd Am. Meeting of AIUM, 1978 p. 108.
Hisanaga, K. et al. "A Trans-Esophageal Real-Time Sector Scanner With An Oil-filled Cell" Proc. 23rd AIUM 1978, p. 47.
Hisanaga, K. et al, "A New Trans-Esophageal Real--Time Linear Scanner and Initial Clinical Results," p. 69, Proc. 23rd AIUM 1978.
Berci, G. et al, "Miniature Black & White TV Camera for Endoscopy and Other Medical Applications," Biomed. Engrg., vol. 7, #3, Apr. 1972.

*Primary Examiner*—Robert W. Michell
*Assistant Examiner*—Francis J. Jaworski

[57] ABSTRACT

Endoscopic method and apparatus are provided for the simultaneous visual and ultrasonic imaging of internal body parts through use of a probe insertable into a body cavity. The probe includes a rectilinear transducer array acoustically coupled to the body through a cylindrical focusing lens having an outer face which conforms to the probe contour. The transducer array is included in a pulsed ultrasonic imaging system of the B-scan type. A tube, which includes a flexible portion adjacent the probe, connects the probe to a control housing containing manually operated control mechanism for bending the flexible tube portion. A control handle extends from the side of the housing for control of bending by the operator. The pulsed ultrasonic imaging system includes pulse generator and pulse receiver means connected to individual elements of the transducer array by coaxial cables extending through the tube. Electronic beam focusing and scanning means for rectilinear B-scan operation are provided for imaging of objects at close distances adjacent the probe. Visual display means are provided for visual display of the ultrasonic image from the B-scan receiver. An optical illuminating and viewing system is provided for optically viewing internal body parts through the probe, which system includes an objective lens and illuminating means adjacent the distal ends of the probe and transducer array. A removable eyepiece at the housing is used for direct viewing by the operator while guiding the probe into desired position in the body cavity. Means also are provided for viewing the optical image by a video camera having an output connected to a monitor adjacent the ultrasonic image display. Consequently, both the optical and ultrasonic images are simultaneously displayable and viewable by the operator.

12 Claims, 7 Drawing Figures

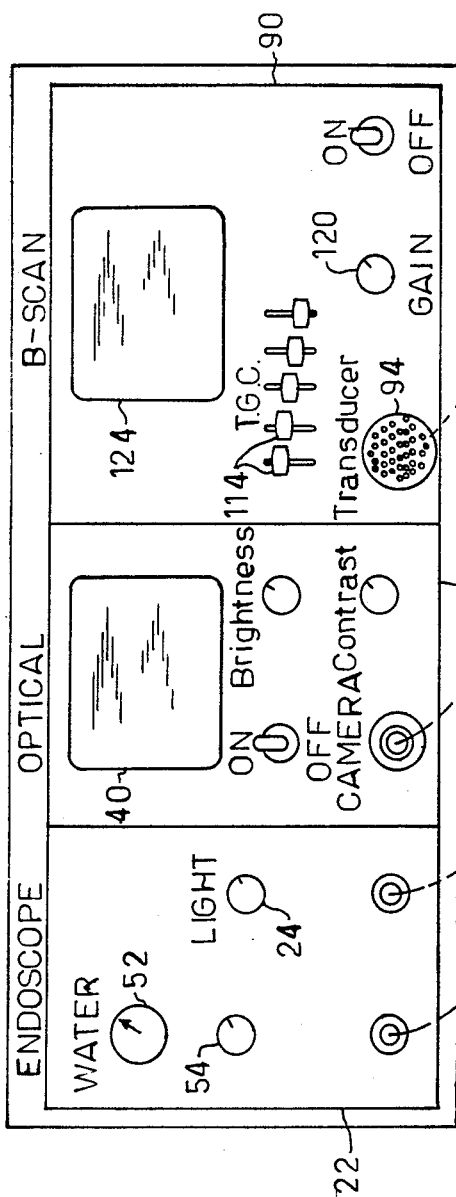
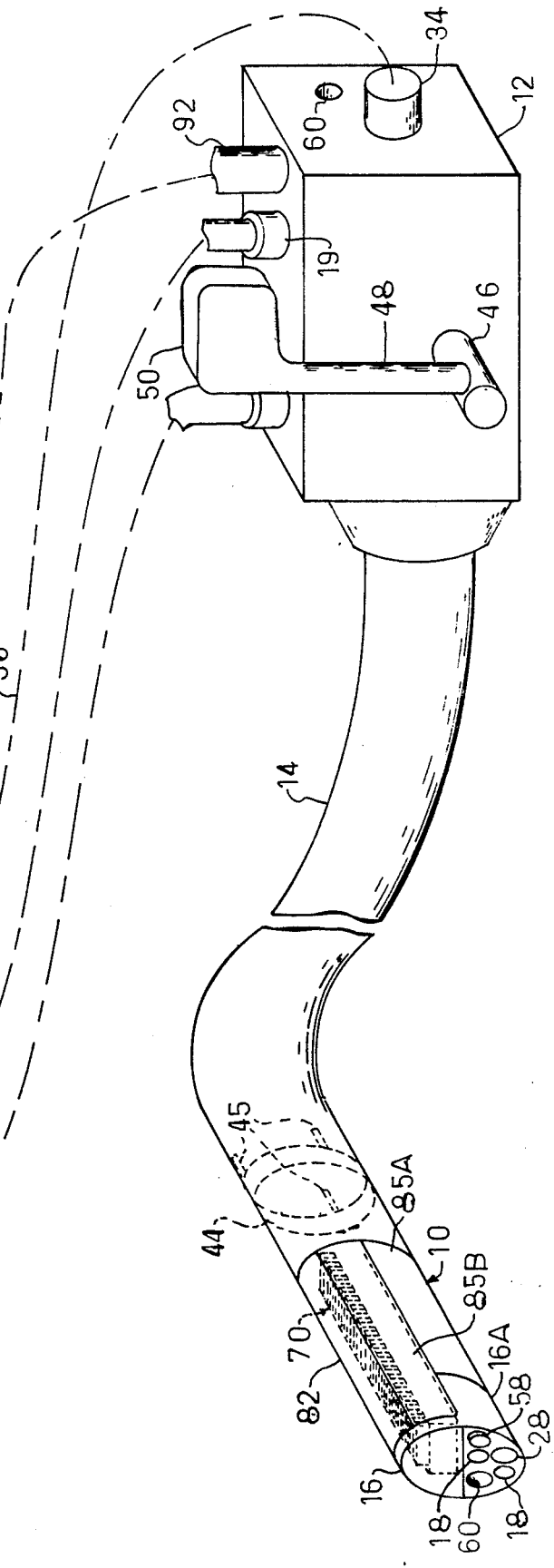

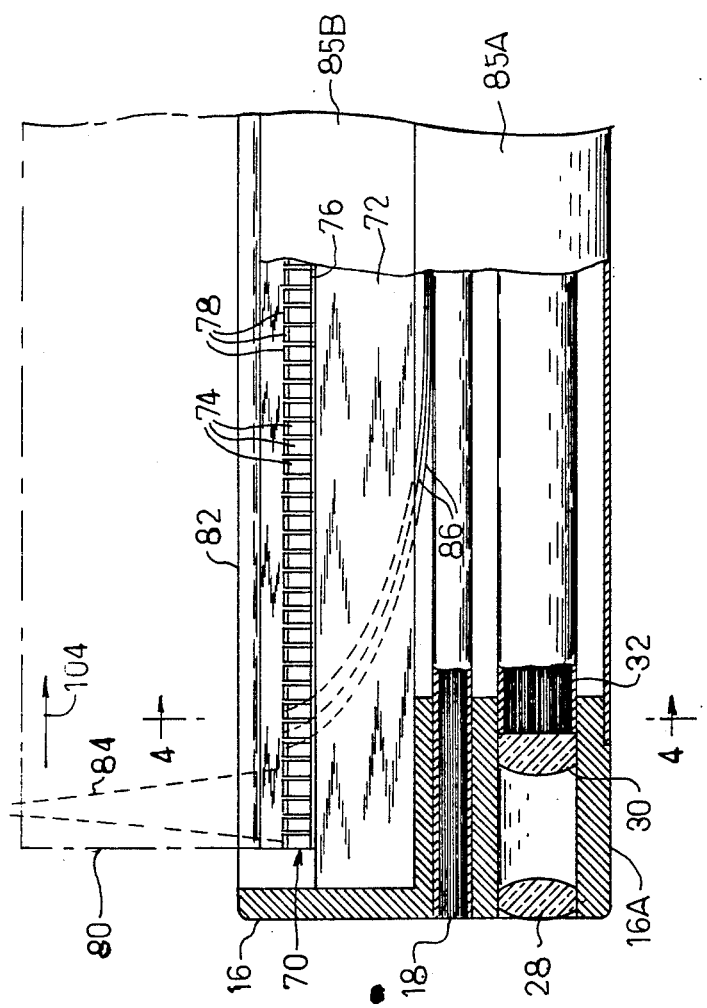
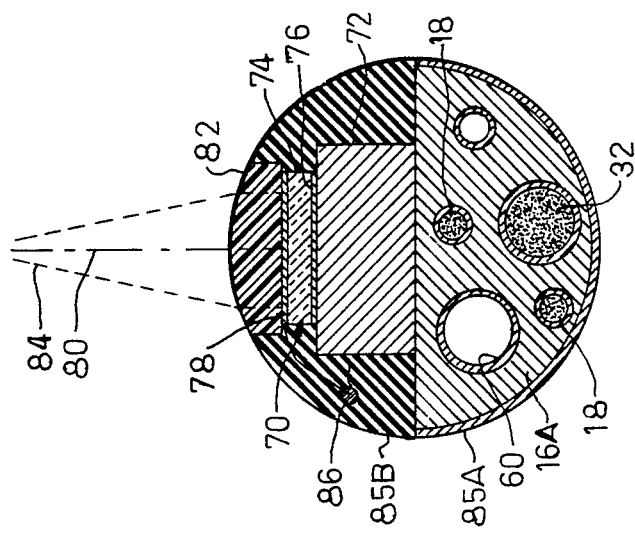
FIG-3
FIG-4

ENDOSCOPIC METHOD & APPARATUS INCLUDING ULTRASONIC B-SCAN IMAGING

ORIGIN OF THE INVENTION

The Government has rights in this invention pursuant to Contact No. 1-CB-74136.

BACKGROUND OF THE INVENTION

Endoscopes for the visual inspection of internal organs of living bodies are well known. They include either a flexible or rigid tube extending between a control housing at the proximal end and a tip or probe at the distal end thereof. A flexible tube portion is included adjacent the probe which is bent under operator control by use of control mechanism at the control housing. Optical illuminating and viewing means are provided which include an objective lens at the probe and an eyepiece at the control housing for use in viewing the cavity surface.

While endoscopes provide the operator with information concerning interior surface conditions, the need for ultrasonic imaging of underlying surfaces has been recognized. In an article entitled A New Trans-digestive-tract scanner with a gastro-fiberscope, by K. Hisanaga and A. Hisanaga, in the Proceedings of the 23rd Annual Meeting of the American Institute of Ultrasound in Medicine, 1978, page 108, an optic-fiber endoscope is shown fitted with a movable transducer for obtaining B-sector-scan images of underlying tissues. However, as noted in the article, the images obtained are of no diagnostic value. Probes containing linear transducer arrays also are known as shown in U.S. Pat. No. 3,938,502 and German Pat. No. 2,305,501. There, circular and rectilinear transducer arrays, respectively are shown. These probes, however, lack optical viewing means which permit the operator to locate the probe at desired locations within the body part. Without such knowledge of transducer location and orientation, any ultrasonic images obtained would be of minimum diagnostic use. Additionally, optical viewing means generally are required for safely guiding the probe during insertion thereof into the body organ to avoid damage and pain to the patient. These probes also lack acoustical cylindrical lens focusing means for beam focusing. Linear array ultrasonic transducers with a cylindrical lens for focusing in one plane normal to electronic beam focusing in a second plane are known as shown in U.S. Pat. No. 3,936,791. There, however, the lens is formed with a concave outer free surface which would not be suitable for use in an endoscopic probe.

SUMMARY OF THE INVENTION AND OBJECTS

It is a general object of this invention to provide an improved probe insertable into a body cavity for use in rectilinear ultrasonic B-scan imaging of internal body parts.

It is another general object of this invention to provide a combination pulsed ultrasonic B-scan imaging system and endoscopic instrument which overcomes the above-mentioned shortcomings and difficulties of the prior art devices.

Another object of this invention is the provision of an ultrasonic imaging system and endoscopic instrument which includes a probe which is readily optically guided to desired locations within body organs, and by means of which high-resolution, real-time, images of underlying tissue are obtained which are useful for diagnostic purposes.

The above and other objects and advantages are achieved by use of an endoscopic instrument having a probe connected by a tube to a control housing. The instrument may include an optical illuminating and viewing system including an objective lens at the probe and an eyepiece at the housing for optically viewing internal surfaces of body parts. At least a portion of the tube adjacent the probe is flexible, and a control handle at the control housing provides means under operator control for bending the same in a desired direction to facilitate guiding the probe into the body part and to locate the same at a desired location therewithin. Ultrasonic imaging of underlying tissue at optically-identified areas is provided by means of a pulsed ultrasonic imaging system of the rectilinear B-scan type. A transducer array is located within the probe adjacent the distal end thereof, and coaxial cables connect individual transducer elements of the array to pulse generator and pulse receiver means of the B-scan system. Means are provided for transmitting and receiving ultrasonic energy using groups of transducer elements in a manner to provide for beam focusing and scanning in the longitudinal plane of the array. Solid focusing lens means of low-velocity material is attached to the face of the array, which lens means has an outer face which conforms essentially to the contour of the outer surface of the probe, for beam focusing in a direction normal to the longitudinal plane of the transducer array. With this arrangement high resolution ultrasonic images are obtained over a range of depths beneath the surface of the body part. The real-time images are displayed at display means readily viewable by the operator. Where the instrument includes an optical viewing system, a closed circuit TV system also is provided which includes a camera responsive to optical images from the probe, and a TV monitor adjacent the B-scan display means. As a result, the optical and ultrasonic images are simultaneously displayed for simultaneous viewing by the operator.

The nature of the present invention will be more fully apparent and understood from a consideration of the following description in light of the drawings wherein like reference characters refer to the same items in the several views.

BRIEF DESCRIPTION OF THE DRAWINGS

In the drawings:

FIG. 1 is a combination elevational and perspective view of an endoscopic instrument and ultrasonic imaging system which embodies the present invention;

FIG. 2 is an elevational view of an eyepiece which may be used with the present system;

FIG. 3 is an enlarged fragmentary elevational view of the probe, with parts thereof being shown broken away for clarity;

FIG. 4 is a sectional view taken along lines 4—4 of FIG. 3;

Figure 5:
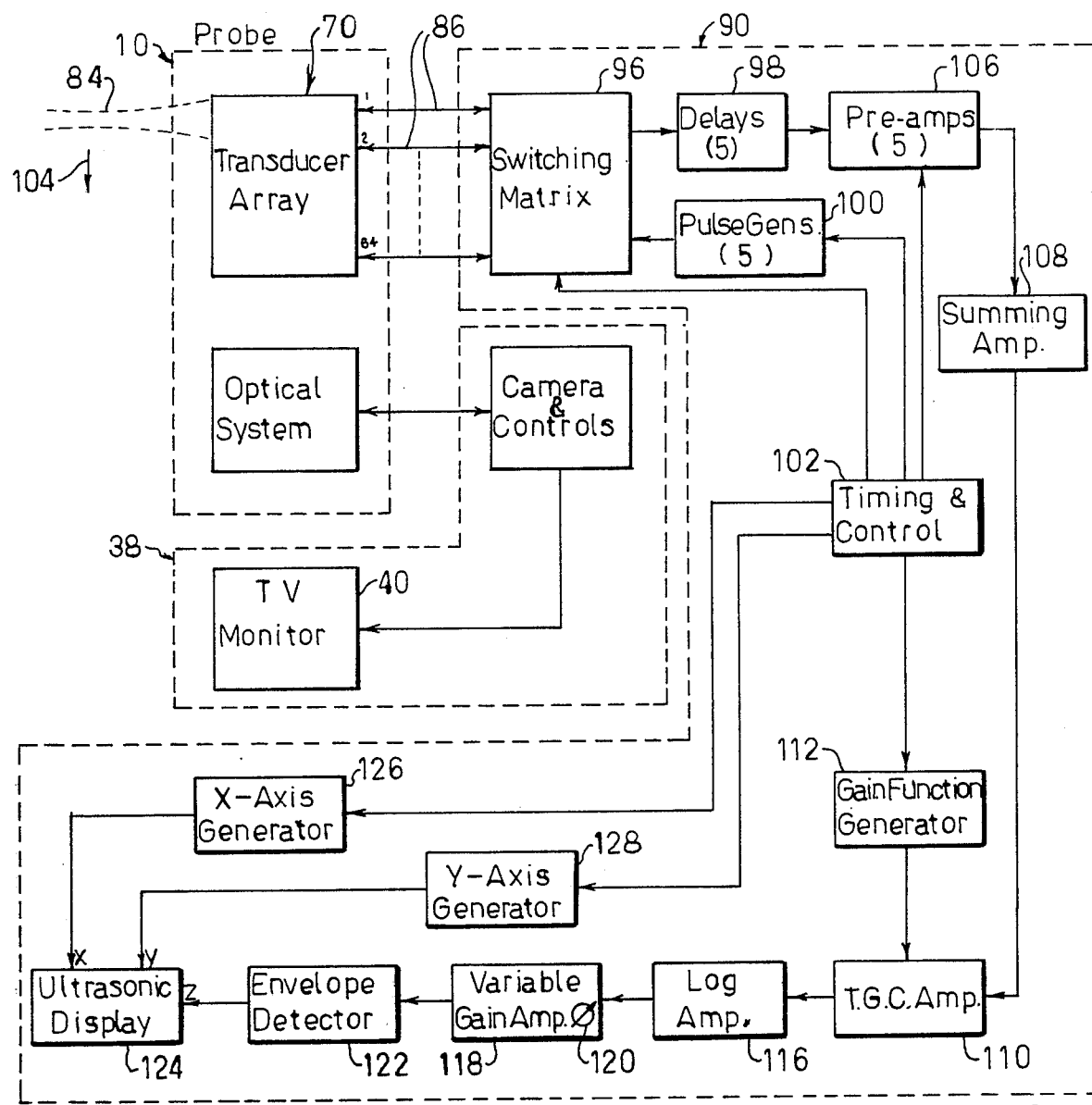
FIG. 5 is a simplified block diagram of the system shown in FIG. 1, including details of an ultrasonic imaging system of the type which is suitable for use in the system.

As noted above, ultrasonic imaging of internal body parts is well known. Also, it is known that not only is the ultrasonic energy attenuated in travel through organs and tissues, but that the attenuation increases with frequency. That is, high frequency signals are attenuated more severely than low frequency signals, or signal components. Consequently, where imaging from the patient's skin of body parts deep within the body is desired, relatively low frequency energy is employed to minimize attenuation. Resolution obtainable, however, is dependent upon the frequency of the energy waves. Consequently, if transmission of ultrasonic energy through substantial amounts of body material is required for imaging the desired body part, it will be apparent that use of relatively low frequency energy is required, thereby limiting resolution. By including the transducer array in an endoscopic probe, high resolution ultrasonic images of internal body parts far removed from the skin may be obtained by operating at high frequencies, on the order of, say, 10 MHz. With the present system, high resolution images of, for example, the pancreas are possible, intragastrically, through the stomach and duodenum walls.

Reference now is made to FIG. 1 wherein the novel endoscopic and ultrasonic imaging system is shown comprising a novel probe 10 connected to housing 12 through a tube 14, at least a portion of which tube adjacent the probe is flexible. The system comprises an endoscope of substantially conventional design and, for purposes of illustration, a flexible endoscope is shown. The probe 10 includes a rigid distal end member, or support block, 16, of generally cylindrical shape at the distal end. The end member is formed, or provided, with a generally semi-cylindrical shape rearwardly extending portion, or member 16A, used for support of portions of an optical illumination and viewing system, and of a transducer array, as described below.

The optical illumination and viewing system is shown comprising light-transmitting fiber bundles 18, 18 which extend axially through the long portion of the supporting block 16 and terminate at the front face thereof. The bundles, which are contained in a protective sheathing, pass rearwardly through the tube 14, into housing 12, and terminate at optical coupling means 19 at one wall of the housing 12. A fiber-optic cable 20 connects the bundles to a suitable source of illumination, not shown, at an endoscopic control unit 22. A light switch and intensity control 24 is provided at the panel of the control unit 22 for illumination control. The illustrated unit 22 also provides a source of fluids such as pressurized air and water, which may be connected to the endoscope. In FIG. 1, only a water source is shown which is connected to the endoscope, for purposes described below.

The optical viewing system includes an objective lens comprising e.g. lens elements 28 and 30 (see also FIG. 3) contained in an axially extending aperture extending through the long portion of the supporting block 16. The one lens element 28, comprising a viewing window is suitably mounted adjacent the front face of the supporting block 16 while the other element 30 is attached to the forward end of a bundle 32 of light-transmitting fibers. From the probe 10, the bundle 32 passes rearwardly through the tube 14 and control housing 12 to an optical connector 34 at the rear of the housing. In FIG. 1 a fiber-optic cable 36 is diagrammatically shown for connection of the viewing system to a video camera, not shown, included in a video display and control unit 38. The camera in control unit 38 comprises an element of a close-circuit TV system which includes visual display means 40 for visual display of objects within view of the objective lens. On-off, brightness, and contrast controls included in conventional closed circuit TV systems are shown at the front panel of the video display and control unit 38.

An eyepiece 42, shown in FIG. 2, may be coupled to the endoscope viewing system through optical coupler 34 after first disconnecting optic-fiber cable 36 therefrom to allow for direct viewing by the operator, instead of viewing at the screen 40. Use of the eyepiece 42 often is preferred during insertion of the probe into the body cavity.

Flexure control means of conventional design may be employed to control bending of the tube 14 adjacent the probe 10. In FIG. 1, a deflector ring 44 is shown in broken lines adjacent the proximal end of the probe 10, which connects through three control wires 45 to flexure control mechanism contained in housing 12. The flexure control mechanism includes a first rotatable shaft 46 extending from the housing, a second rotatable shaft 48 extending radially from the first shaft 46, and a handle 50 at the free end of the shaft 48. Simultaneous rotation of the two shafts 46 and 48 by operation of the handle 50 is possible for bending of the probe 10 in any desired direction relative to the flexible distal end of tube 14.

As noted above, the unit 22 also provides a source of water for the endoscope. Water pressure gauge 52 displays the pressure of water supplied to the endoscope, and control 54 is used for setting the pressure at the desired level. Water is supplied over conduit 56 to the housing 12 and from there is fed through the tube 14 and probe 10 to a nozzle head 58 protruding slightly from the face of the probe. Water from the nozzle flows past the ends of illuminating fiber bundles 18, 18 and over lens element 28 to maintain the same clear of mucus, or the like. In the illustrated arrangement, a guide channel 60 also is provided which extends from the tip of the probe 10 to unit 12, opening to the exterior thereof, through which tools of various types, not shown, may be passed. It here will be noted that with the novel probe of this invention the various endoscopic channels described above extend through the generally semicylindrical portion 16A of the supporting block 16, and terminate within approximately a substantially semicircular area of the tip face. The other half, approximately, of the generally cylindrically shaped probe is occupied by a rectilinear ultrasonic transducer array, identified generally by reference numeral 70. With the illustrated side-by-side positioning of the transducer array and endoscopic channels, and by locating the distal end of the transducer array adjacent the distal end of the probe, a probe of minimum overall length is provided for ease of insertion into a patient.

The illustrated transducer array, best seen in FIGS. 3 and 4 of the drawings, is shown comprising a rectangular base 72 of conducting material to which piezoelectric transducer elements 74 of the array are secured. Electrodes 76 and 78 are provided at respective opposite faces of the piezoelectric material 74. For purposes of illustration only, and not by way of limitation, the array may be constructed from say, a 3 cm. by 0.5 cm. body of piezoelectric material having electrodes disposed at opposite faces thereof, which piezoelectric body is uniformly polarized normal to said opposite, parallel, electrode-covered faces. The piezoelectric body, with electrodes disposed thereon, is attached to the base 72 by use of an electrical conducting cement for electrical connection thereto. The base 72 is made of an acoustic damping material for lowering the acoustic Q-factor of the array so that short acoustic pulses may be generated and received, a requirement for good range resolution. After bonding to the base 72, the piezoelectric material is diced into, say 64 closely spaced elements to form the illustrated rectilinear array. With the above-dimensions, and suitable thickness dimension, the transducer elements may be made to operate at a frequency in the range of, say, 8–12 MHz. The distal end of the base 72 of the transducer array is attached, as by bonding, to the end member 16, and means, not shown, support the proximal end of the transducer array within the probe. It will be seen that the longitudinal plane 80 of the transducer array extends longitudinally of the probe.

The illustrated transducer means is provided with focusing means 82 for focusing of the beam 84 in a plane normal to the longitudinal plane 80. The illustrated focusing means 82 comprises a cylindrical lens having one face attached to the face of the transducer array, and an outer face which conforms, essentially, to the cylindrical contour of the outer surface of the probe. Here, the outer face is of generally, convex shape to not only conform to the probe curvature, but also to provide for good contact with the internal body part. Where the probe is used intragastrically, for example, the contour provides good contact with the stomach and intestinal mucosa. As seen in FIGS. 1 and 4, the probe includes a generally semi-cylindrical shaped tubular housing section 85A at the optical portion thereof. Potting material 85B fills voids in the housing section 85A and is molded about the transducer array 70 to house the same. By way of example, the housing portion 85B may be formed of an electrical potting resin which may be applied by use of a suitable mold, and cured in place. Together, elements 85A and 85B comprise a generally cylindrical-shaped housing for the probe, through which the cylindrical focusing lens means 82 extends. In FIG. 3, potting material 85B is shown removed from the broken away portion of the probe to clearly illustrate other internal probe elements.

Figure 7:
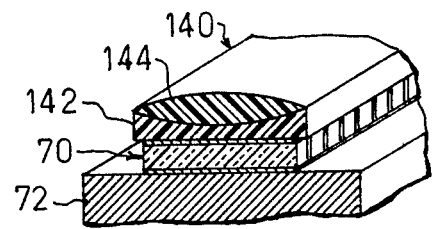
FIG. 7 is a sectional view of a composite cylindrical acoustical focusing lens of the type which may be used in the probe of this invention.

As is understood, the velocity of propagation of acoustic waves in soft body tissue is approximately the same as in water. To provide for the illustrated focusing by the cylindrical lens means 82, the lens is made of a material having a velocity of propagation of acoustic waves which is substantially less than the velocity in the soft tissue, and in water. One such material which may be used in the fabrication of the lens includes "Sylgard" 184 manufactured by Dow Corning Corporation. Other low-velocity materials which are suitable for use may be used. In the illustrate embodiment, the focusing means comprises a single lens element. Obviously, a composite lens made up of a plurality of lens elements may be used, such as shown in FIG. 7 and described below. Also, the lens surface may be coated with an antireflection material, not shown, to minimize internal reflections of acoustic waves. Focusing of the beam 84 by the lens 82 in a plane normal to the longitudinal plane 80 of the transducer array is illustrated in FIG. 4 of the drawing. Obviously, the outer surface of the lens 82, as well as the remainder of the probe 10 and tube 14 surfaces which, in use, will be in contact with body secretions, must be formed of stable material which is nonreactive with such body secretions.

The rectilinear transducer array 70 is included in a pulsed ultrasonic B-scan imaging system operating in a rectilinear beam scanning mode as opposed, say, to sector scanning. Although sector scan systems have the advantage that a small transducer array can provide a large field of view far from the array, the field of view is small and the resolution is poor close to the array. By using a rectilinear scan, all lines of the image are parallel, and tissue near the transducer array is readily imaged. Reference now also is made to FIG. 5 which includes a block diagram showing of a B-scan system of conventional design and which may be used in the present arrangement. As noted above, a 64 element transducer array 70 may be used, in which case 64 microminiature coaxial cables 86 are used to connect the transducer elements to the B-scan transmitter/receiver identified generally by reference numeral 90. The 64 coaxial cables 86 are loosely bound within sheath 92, seen in FIG. 1, to allow for repeated bending without damage thereto. In the illustrated arrangement, the bundle of cables simply extends through the interior of the control housing 12, and the individual cables thereof are attached by connector 94 (FIG. 1) to the B-scan transmitter/receiver 90. To avoid unnecessary deleterious effects on signals carried by the cables, no connectors, or terminals, are included at the housing 12. Obviously, the bundle of cables 92 may be extended from the side of the flexible tube 14 adjacent the housing 12 for direct coupling thereof to the transmitter/receiver 90 without passage through the housing 12, if desired.

As seen in FIG. 5, the transducer elements are connected to a switching matrix 96 by means of which selected groups of adjacent transducer elements are connected to delay means 98, or pulse generating means 100. For purposes of illustration only, groups of five transducer elements are employed, and each delay means 98 and pulse generating means 100 comprise five such individual devices. A timing and control unit 102 is connected to the switching matrix for selecting groups of transducer elements to be activated. The timing and control unit also controls the timing of the operation of the five pulse generators 100 for excitation of the elements of the selected group in phased relation for focusing of the beam 84 in the longitudinal plane of the transducer array. In FIGS. 3 and 5, such focusing by proper excitation of the first five transducer elements in the array is illustrated. The energized group is shifted along the array for beam scanning in the direction of arrow 104.

Reflected ultrasonic signals from discontinuities within the pulse-insonified body part as received by the same group of transducer elements and supplied through switching matrix 96 and delay means 98 to pre-amplifier means 106. The five preamplifiers of pre-amplifier means 106 are of the low-noise, broad-band, high dynamic range type having good linear gain characteristics over a wide input signal strength range. The delays are selected to provide focusing of the beam pattern in the longitudinal plane 80 of the transducer array during receiver operation. It will be seen, then, that phased array operation of the transducer array is provided during both transmitting and receiving operation for beam focusing. Shifting of the selected groups of active transducer elements follows the pulse-echo receiving period to provide for the above-mentioned rectilinear beam scanning operation. By shifting in increments of one transducer element, a total of 60 scan lines are provided. Obviously, the system may be operated with groups using different numbers of transducer elements. Also, groups of both odd and even numbers of transducer elements may be employed for shifting in increments of one-half a transducer element width, as is well understood.

The preamplifier outputs are fed to a summing amplifier 108 having an output related to a weighted sum of the inputs. The summing amplifier output is supplied to a time variable gain amplifier 110 having a gain characteristic which varies as a function of time to compensate for the loss of signal amplitude as it traverses the tissue. In the illustrated arrangement, the gain of the amplifier 110 is varied in accordance with the output from a gain function generator 112. A synchronizing signal is supplied to the gain function generator 112 from the timing and control unit 102 for initiating operation thereof a predetermined time period following operation of the pulse generators 100. The gain function generator 112 simply may comprise a ramp generator with an output signal which functions to increase the gain of the amplifier 110 in proportion to range in a manner to offset the loss of signal caused by acoustic absorption within the subject. In the present arrangement, an adjustable function generator 112 is used having a plurality of controls 114 accessible at the front of the B-scan unit 90 (see FIG. 1) for control of the shape of the generator output. The setting of each of the five controls 114 determines the amplifier 112 gain during one-fifth of the echo signal duration thereby permitting the operator to tailor the B-scan display as desired. Adjustable gain function generators for control of variable gain amplifiers are well known and require no detailed description.

The output from the time gain control amplifier 110 is supplied to a broad band compression amplifier 116 comprising, for example, a DC coupled log amplifier. The compression amplifier 116 is followed by a variable gain amplifier 118 having a gain control 120 for setting the gain thereof.

The variable gain amplifier 118 output is detected by an envelope detector 122 comprising, for example, a full wave rectifier followed by a low pass filter, the detector output signal being related to the envelope of the broad band high frequency signal output from the amplifier 118. The envelope detector output is supplied to the ultrasonic image display device 124 comprising a cathode ray tube. Generally, a compression amplifier not shown, is included in the connection of the detector 122 output signal to the cathode ray tube 124 for matching the detected signal with characteristics of the cathode ray tube 124 for proper display of the entire signal range. The detector output is applied as an input to the control grid of the cathode ray tube for intensity, Z-axis, control of the electron beam.

For B-scan operation, cathode ray tube beam deflection in the X, or horizontal, direction is proportional to the position of the beam 84 along the scanning path. X-axis generator 126, triggered by a synchronizing signal from the timing and control unit 102, provides a stepped signal output which is supplied to the horizontal deflection system of the cathode ray tube 124 for shifting the trace on the cathode ray tube in accordance with the position of the ultrasonic beam 84.

Vertical, or Y-axis, deflection of the cathode ray tube beam is provided by a ramp generator 128 which is triggered by an output from the timing and control unit 102 a predetermined time period following transmitter operation. The ramp generator 128 output is supplied to the vertical deflection system of the cathode ray tube 124 for vertical scanning of the trace. It will be apparent, then, that a rectilinear B-scan ultrasonic image of the body part lying within the longitudinal plane 80 of the transducer array 70 contained in the probe 10 is provided at the face of the cathode ray tube 124. As seen in FIG. 1, the ultrasonic image display means 124 is located adjacent the TV monitor, or display means, 40. The simultaneous displays of the optical and ultrasonic images are readily viewable by the operator to aid the operator in properly positioning the probe within the body cavity for obtaining the desired ultrasonic images. Obviously, recording means, not shown, may be included for recording of the real-time ultrasonic images provided by the B-scan system to preserve the same for subsequent examination. Similarly, a recording of the optical images may be made, if desired, from, say, the video camera signal outputs. Also, if desired, the B-scan receiver output may be supplied to a scan converter, not shown, for conversion of the ultrasonic image signals to signals having a conventional television format, in which case the scan converter output may be supplied to a conventional television monitor, not shown, for display. In this case, a recording of the scan converter output may be made and used with conventional TV play-back and monitor means for subsequent display of the ultrasonic images.

Although the operation of the endoscopic system of this invention is believed to be apparent from the above description, a brief description thereof with reference also to FIG. 6 now will be given. For purposes of illustration, and not by way of limitation, the present endoscopic apparatus is shown, in FIG. 6, employed in the gastrointestinal system of a patient. The detection of malignancy outside the tubular gastrointestinal tract is difficult, and the diagnosis of cancer involving the pancreas and pancreatic bed, peritoneal cavity, and mesentery is particularly difficult. However, the proximity of the pancreas to the stomach and duodenum make it and its surrounding structures ideal for high-resolution ultrasonic visualization with the ultrasonic probe of the present invention.

Figure 6:
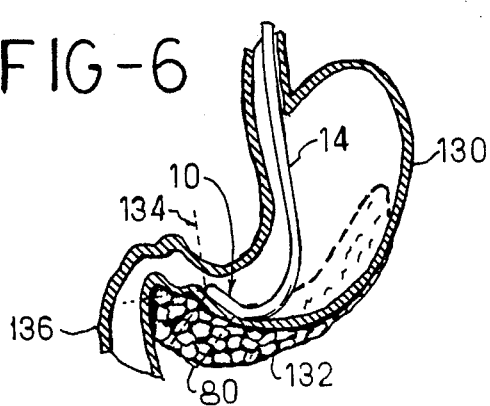
FIG. 6 is a diagrammatic view showing the probe positioned within a stomach for ultrasonic examination of the adjacent pancreas.

In FIG. 6 the endoscopic ultrasonic probe 10 is shown inserted into the patient's stomach 130. Conventionally, optical guidance is relied upon to guide the probe through the esophagus and into desired placement within the gastrointestinal tract. Many endoscopists prefer using the eyepiece 42 (FIG. 2) when guiding the probe into desired position, in which case the light transmitting fiber cable 36 (FIG. 1) is removed and the eyepiece 42 is attached to the endoscope by use of the connector assembly 34. With the eyepiece 42 in place, the endoscopic ultrasonic probe 10 is guided into desired position for ultrasonic imaging of underlying soft tissue. In FIG. 6, the probe 10 is shown advanced to the greater curvature of the stomach 130 adjacent the pancreas 132. Through manipulation of the probe, firm contact of the cylindrical lens 82 of the transducer array with the mucosa is effected enabling ultrasonic scanning to proceed. At this time, the eyepiece 42 may be removed from the endoscope and replaced by optical fiber cable 36 for connection of the optical system to the closed circuit television for display of the optical image at the screen 40 of the TV monitor. Both the optical image and ultrasonic image are simultaneously displayed, and viewable, by the operator. In FIG. 6 the ultrasonic imaging plane 80 is identified, together with the optical viewing angle 134. By proper manipulation of the probe 10, ultrasonic scanning of the pancreas may be provided from the tail area thereof to the pancreatic head through the stomach wall. By maneuvering the probe into the duodenum 136, additional ultrasonic imaging of the head of the pancreas 132 from different locations is possible. High resolution ultrasonic images which extend from a position close to the surface of the probe to a depth of approximately 4 cm. are possible. With a transducer array 70 having a length of 3 cm., for example, a 3 cm. wide×4 cm. deep field of view is possible. Also, by operating at, say 10 MHz, good lateral resolution of approximately 0.5 mm., average, and good range resolution of approximately 0.5 mm., are possible.

As noted above, composite focusing lens means may be used in place of lens means 82 shown in FIGS. 1, 3 and 4 and described above. Reference now is made to FIG. 7 wherein a composite cylindrical lens 140 for use herein is shown, which includes first and second lens elements 142 and 144. The first lens element 142 has a planar face bonded to the face of the transducer array 70, and an opposite concave face. The second lens element 144 has opposite convex surfaces, one of which is bonded to the concave face of the first element 142. The outer convex face of the outer lens element conforms generally to a curved portion of the contour of the outer surface of the probe, not shown in FIG. 7. The first lens element 142 is formed of a material having a velocity of propagation of acoustic waves which is substantially greater than the velocity of propagation of acoustic waves in soft body tissue, and in water. The second lens element 144 is formed of a material having a velocity of propagation of acoustic waves which is no greater, but preferably is substantially less, than the velocity of propagation in soft body tissue. It will be apparent that by using a low velocity material for the outer lens 144, focusing action at both the soft tissue-lens 144 interface, and lens 144-lens 142 interface, is provided. Also, as with the lens means 82, good contact between the outer convex face of lens element 144 and soft body tissue is possible because of the convex lens face.

The invention having been described in detail in accordance with requirements of the Patent Statutes, various other changes and modifications will suggest themselves to those skilled in the art. For example, instead of the illustrated forward looking optical system, the probe may be provided with a side, or with partially forward and side looking optical viewing means. Also, for use in different body cavities, a rigid tube endoscope, rather than the flexible tube 14 endoscopic instrument may be used, in which case, simple optical telescope and illumination means, without the need for the light transmitting fiber cables may be employed in the construction. Also, as noted above, although electronic rectilinear B-scan imaging is required for satisfactory ultrasonic real-time imaging, numerous apparatii for implementing the same are known, and the apparatus shown in FIG. 5 simply is for purposes of illustration only, and not by way of limitation. Use of the illustrated sequenced, dynamically focused, rectilinear array requires a significant amount of preprocessing electronics. To maximize dynamic range, these circuits should be located as close to the transducer array as possible. The present invention contemplates locating such circuitry in the probe 10 itself, using integrated circuit chips. Present, commercially available, chips are not well suited to such use, and custom fabricated electronics which are suitable would be very expensive. Nevertheless, the use of suitable preprocessing microelectronic circuitry within the probe is entirely feasible, and is contemplated by the present invention.

It is intended that the above and other such changes and modifications shall fall within the spirit and scope of the invention as defined in the appended claims.

We claim:

1. An endoscopic probe for use in a system for visually examining and for ultrasonically imaging internal body parts, said probe comprising,
    a substantially cylindrical shaped elongated housing having forward and rear ends at the respective distal and proximal ends thereof and a longitudinal axis, said housing including a distal end member at the forward end thereof,
    means forming a plurality of longitudinally extending apertures through said distal end member at a first substantially semicylindrical portion of said housing for use in optically imaging internal body parts, and
    a longitudinally extending rectilinear ultrasonic transducer array including a plurality of adjacent transducer elements within the probe housing, said transducer array being positioned rearwardly the forward end of of said distal end member at a second substantially semicylindrical portion of said housing substantially opposite said first semicylindrical portion for use in ultrasonically imaging internal body parts.

2. An endoscopic probe as defined in claim 1 wherein the distal end of said distal end member is of substantially cylindrical shape.

3. An endoscopic probe as defined in claim 2 including a rearwardly extending substantially semicylindrical shaped member integrally formed with said distal end member for support of said transducer array.

4. An endoscopic probe as defined in claim 1 wherein said unitary housing has a substantially cylindrical-shaped outer surface, said probe including cylindrical focusing lens means having one face attached to the transducer elements of the transducer array and having an outer face forming a portion of the outer surface of said probe housing.

5. An endoscopic probe as defined in claim 4 wherein said cylindrical focusing lens means is formed of solid material having a velocity of propagation of acoustic waves which is substantially less than the velocity of propagation of acoustic waves in soft body tissue.

6. An endoscopic probe for insertion into a body cavity for use in a system for visually examining and ultrasonic imaging internal body parts comprising,
    a housing having forward and rear ends at the respective distal and proximal ends thereof, said housing having a substantially cylindrical-shaped outer surface with a longitudinal axis,
    means at the rear end of the housing for attachment thereof to an elongated tube,
    a rectilinear transducer array inside said housing extending substantially parallel to the longitudinal probe housing axis and having forward and rear ends adjacent the respective forward and rear ends of the housing, said array comprising a plurality of transducer elements for directing pulses of ultrasonic energy along a beam into body parts,
    cylindrical focusing lens means having one face attached to said transducer face for beam focusing in a plane normal to the longitudinal plane of the transducer array, the outer face of said cylindrical focusing lens means being convex and forming a portion of the outer surface of said housing, and an optical system for use in visually examining internal body parts including objective lens means inside said housing adjacent the forward end of the transducer array at the forward end of the housing.

7. A probe as defined in claim 6 wherein said cylindrical focusing lens means is formed of a solid material having a velocity of propagation of acoustic waves which is substantially less than the velocity of propagation of acoustic waves in soft tissue.

8. An endoscopic system for visual and ultrasonic imaging of body parts comprising, an endoscope comprising an elongated tube and probe at the distal end of the tube insertable into a body organ, a television system comprising a camera located at a distance from said endoscope, means for optically coupling said television camera to said endoscope and thence through said elongated tube to said probe for optically viewing the organ from the probe, and a monitor electrically coupled to said camera for visually displaying an image of the viewed organ, and a pulsed rectilinear B-scan ultrasonic imaging system comprising, a rectilinear ultrasonic transducer array inside said probe, pulse transmitter/receiver means connected to said transducer array for pulse energization of the transducer array for generating ultrasonic wave pulses and for processing signals received from the transducer array, and visual display means for B-scan display of the processed signals for the simultaneous display of ultrasonic and video images at said visual display means and monitor, respectively.

9. An endoscopic system as defined in claim 8 wherein said visual display means and monitor are adjacent each other for simultaneous viewing.

10. In a combination visual and ultrasonic real-time B-scan imaging method which includes the use of an endoscopic system which includes an endoscopic probe insertable into a body organ, which probe includes a rectilinear ultrasonic transducer array and objective lens of optical telescope means, the steps comprising, generating by use of said transducer array, recurrent ultrasonic wave pulses to insonify a section of a body part adjacent the body organ into which said probe is inserted, receiving reflected wave pulses and converting the same to corresponding electrical signals by use of said transducer array, displaying a real-time rectilinear B-scan image of an insonified section of the body part, viewing, through said optical telescope means by use of video camera means, optical images of a portion of the interior of the body organ into which the probe is inserted, displaying the output from said video camera means at visual display means, and locating said B-scan image display means and visual display means adjacent each other for substantially simultaneous viewing by the operator of the endoscopic system.

11. In a combination visual and ultrasonic real-time B-scan imaging method as defined in claim 10 which includes locating the video camera a distance from said endoscopic probe and viewing said optical images through optical fiber means included in said optical telescope means and connecting said optical telescope means to the video camera.

12. A probe for use in an endoscopic system for ultrasonically imaging and optically viewing internal body parts, said probe comprising, unitary housing means having a substantially cylindrical-shaped outer surface with a longitudinally extending axis, a forward distal end, and a rearward proximal end connected to an elongated tube for use in inserting the housing means into a body organ, ultrasonic transducer means fixedly mounted inside said housing means at one side of the longitudinal axis thereof for use in generating ultrasonic waves and receiving reflected ultrasonic waves for ultrasonic image examination of internal body parts with said transducer inside said housing means, and optical means inside said housing means to a side of the longitudinal axis diametrically opposite said ultrasonic transducer means for use in illuminating and visually examining internal body parts, said optical means including a viewing window adjacent the forward distal end of said housing means forwardly of said ultrasonic transducer means.

* * * * *